US010877297B2

(12) United States Patent
Rousseau et al.

(10) Patent No.: US 10,877,297 B2
(45) Date of Patent: Dec. 29, 2020

(54) MONITORING COMPONENT OF THE POSITION OF A HEAD MOUNTED DEVICE

(71) Applicant: Essilor International, Charenton-le-Pont (FR)

(72) Inventors: Denis Rousseau, Charenton-le-Pont (FR); Konogan Baranton, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 418 days.

(21) Appl. No.: 15/563,107

(22) PCT Filed: Apr. 1, 2016

(86) PCT No.: PCT/EP2016/057277
§ 371 (c)(1),
(2) Date: Sep. 29, 2017

(87) PCT Pub. No.: WO2016/156600
PCT Pub. Date: Oct. 6, 2016

(65) Prior Publication Data
US 2018/0348547 A1 Dec. 6, 2018

(30) Foreign Application Priority Data
Apr. 2, 2015 (EP) .................... 15305494

(51) Int. Cl.
*G02C 11/00* (2006.01)
*G02B 27/01* (2006.01)
*A61B 5/00* (2006.01)
(52) U.S. Cl.
CPC ............ *G02C 11/10* (2013.01); *G02B 27/017* (2013.01); *G02B 27/0172* (2013.01);
(Continued)

(58) Field of Classification Search
CPC .......... G02C 11/10; G02C 7/04; G02C 7/101; G02C 11/04; G02C 7/083; G02C 11/00;
(Continued)

(56) References Cited

U.S. PATENT DOCUMENTS 4,873,994 A 10/1989 Anger et al.
6,115,177 A 9/2000 Vossler
(Continued)

FOREIGN PATENT DOCUMENTS

EP 2 980 628 A1 2/2016
WO 2012/011893 A1 1/2012

OTHER PUBLICATIONS

International Search Report and Written Opinion dated Oct. 18, 2016, in PCT/EP2016/057277 filed Apr. 1, 2016.

*Primary Examiner* — Collin X Beatty
*Assistant Examiner* — Grant A Gagnon
(74) *Attorney, Agent, or Firm* — Oblon, McClelland, Maier & Neustadt, L.L.P.

(57) ABSTRACT

A monitoring component for monitoring relative position of a head mounted device and a user of the head mounted device, the head mounted device including at least one sensor, the monitoring component including: a memory configured to store computer executable code, and a processor configured to execute the computer executable codes stored in the memory of: a communication code configured to receive data from the head mounted device indicative of at least one feature sensed by the at least one sensor of the head mounted device, an information generating code configured to generate an information indicative of the relative position of the head mounted device and the user of the head mounted device based at least on the data received from the head mounted device.

26 Claims, 2 Drawing Sheets

(52) U.S. Cl.
CPC ........ *G02B 27/0179* (2013.01); *A61B 5/6803* (2013.01); *A61B 5/6844* (2013.01); *G02B 2027/014* (2013.01); *G02B 2027/0138* (2013.01); *G02B 2027/0178* (2013.01); *G02B 2027/0187* (2013.01)

(58) Field of Classification Search
CPC ........ G02C 11/06; G02C 5/143; G02C 7/049; G02C 5/14; G02C 5/001; G02C 7/02; G02C 7/081; G02C 7/085; G02C 2200/02; G02C 5/02; G02C 7/022; G02C 7/086; G02C 7/16; G02C 5/22; G02C 7/021; G02C 7/12; G02C 11/08; G02C 2200/08; G02C 2202/16; G02C 2202/22; G02C 3/003; G02C 7/00; G02C 7/046; G02C 7/06; G02C 7/08; G02C 7/088; G02C 7/104; G02C 9/00; G02C 11/12; G02C 13/00; G02C 13/001; G02C 13/003; G02C 13/005; G02C 13/006; G02C 2200/28; G02C 2202/04; G02C 2202/12; G02C 2202/18; G02C 2202/20; G02C 2202/24; G02C 3/00; G02C 3/02; G02C 3/04; G02C 5/008; G02C 5/04; G02C 5/10; G02C 5/12; G02C 5/146; G02C 5/16; G02C 5/20; G02C 5/2227; G02C 7/061; G02C 7/066; G02C 7/102; G02C 7/105; G02C 7/14; G02C 9/02; G02C 9/04; G02B 2027/0178; G02B 27/017; G02B 27/0172; G02B 2027/0138; G02B 27/0176; G02B 2027/014; G02B 27/0093; G02B 1/043; G02B 2027/0156; G02B 2027/0118; G02B 2027/0187; G02B 27/0101; G02B 5/30; G02B 2027/0127; G02B 2027/0134; G02B 27/022; G02B 27/2264; G02B 7/28; G02B 2027/011; G02B 2027/0112; G02B 2027/0123; G02B 2027/013; G02B 2027/0132; G02B 2027/0141; G02B 2027/0152; G02B 2027/0159; G02B 2027/0169; G02B 21/24; G02B 2207/123; G02B 23/12; G02B 26/026; G02B 26/06; G02B 26/10; G02B 27/0025; G02B 27/01; G02B 27/0149; G02B 27/0179; G02B 27/028; G02B 27/2207; G02B 27/2214; G02B 27/2221; G02B 27/2228; G02B 27/646; G02B 3/0081; G02B 3/12; G02B 3/14; G02B 5/18; G02B 5/1842; G02B 5/1861; G02B 5/32; G02B 7/1824; G02B 7/285; G02B 7/365; A61B 5/6821; A61B 3/10; A61B 3/113; A61B 5/14532; A61B 5/14546; A61B 5/6803; A61B 3/101; A61B 5/0002; A61B 5/0059; A61B 5/02438; A61B 5/1103; A61B 5/14507; A61B 5/6814; A61B 2560/0214; A61B 2560/0223; A61B 3/0008; A61B 3/028; A61B 3/0285; A61B 3/04; A61B 3/1015; A61B 3/14; A61B 3/152; A61B 5/0008; A61B 5/0017; A61B 5/0026; A61B 5/0042; A61B 5/01; A61B 5/015; A61B 5/0205; A61B 5/02055; A61B 5/021; A61B 5/0476; A61B 5/0537; A61B 5/11; A61B 5/1112; A61B 5/145; A61B 5/14517; A61B 5/14539; A61B 5/14542; A61B 5/14551; A61B 5/14553; A61B 5/1486; A61B 5/18; A61B 5/4064; A61B 5/412; A61B 5/72; A61B 5/7235; A61B 5/7271; A61B 5/742; A61B 5/7445; A61B 5/746
USPC ......................................................... 351/158
See application file for complete search history.

(56) References Cited

U.S. PATENT DOCUMENTS

| | | |
|---|---|---|
| 2011/0071416 A1 | 3/2011 | Terada et al. |
| 2012/0056847 A1 | 3/2012 | Milford |
| 2013/0235169 A1 | 9/2013 | Kato et al. |
| 2014/0088372 A1 | 3/2014 | Saeedi et al. |
| 2014/0088881 A1 | 3/2014 | Saeedi et al. |
| 2014/0200734 A1 | 7/2014 | Krenik |
| 2014/0228652 A1 | 8/2014 | Terada et al. |
| 2016/0034032 A1 | 2/2016 | Jeong |
| 2016/0157778 A1 | 6/2016 | Terada et al. |

| Sensor 46 | Sensor 45 | Sensor 44 | Sensor 43 | Sensor 42 | Sensor 41 | HMD position |
|---|---|---|---|---|---|---|
| off | on | on | on | off | off | Normal |
| on | on | on | off | off | off | Down |
| off | off | on | on | on | off | Up |
| off | off | off | off | off | off | Not worn |

MONITORING COMPONENT OF THE POSITION OF A HEAD MOUNTED DEVICE

FIELD OF THE INVENTION

The invention relates to a monitoring component for monitoring the relative position of a head mounted device and a user of the head mounted device. The invention further relates to a head mounted device comprising at least one sensor and a communication unit. The invention finally relates to system for monitoring the relative position of a head mounted device and a user of the head mounted device

BACKGROUND OF THE INVENTION

Head mounted devices are more and more complex so as to provide more and more information and/or services to the wearer or to thirds parties.

With such increase of the complexity of the head mounted devices, there is a need to monitor accurately the relative position of the head mounted device and the user of such head mounted device.

Thus there is a need for monitoring the relative position of a head mounted device and a user of the head mounted device.

One object of the present invention is to provide a monitoring component allowing monitoring the relative position of a head mounted device and a user of the head mounted device.

SUMMARY OF THE INVENTION

To this end, the invention proposes a monitoring component for monitoring the relative position of a head mounted device and a user of the head mounted device, the head mounted device comprising at least one sensor, the monitoring component comprising:
a memory configured to store computer executable code, and
a processor configured to execute the following computer executable codes stored in the memory:
  a communication code configured to receive data from the head mounted device indicative of at least one feature sensed by the at least one sensor of the head mounted device,
  an information generating code configured to generate an information indicative of the relative position of the head mounted device and the user of the head mounted device based at least on the data received from the head mounted device.

Advantageously, the monitoring component according to the invention allows monitoring the relative position of a head mounted device and a user of the head mounted device based on a feature sensed by at least one sensor of the head mounted device.

Monitoring the relative position is advantageous in many manners. For example, the head mounted device may generate information or services to the user of the head mounted device or to a third party and such information or services may depend on the relative position of the head mounted device and the user.

According to further embodiments which can be considered alone or in combination:
the head mounted device further comprises a memory in which the received data are stored over time and the information is indicative of the evolution over time of the relative position of the head mounted device and the user of the head mounted device; and/or
the information generating code is configured to generate information using statistical analysis of the data received from the head mounted device and stored over time; and/or
the information generating code is configured to provide a recommendation data based at least on the data received from the head mounted device; and/or
the recommendation data includes a lens design recommendation and/or an ophthalmic lens recommendation and/or an alert indicative of wearer's vision state and/or an activation of at least one functionality on the head mounted device and/or an access to a service offer; and/or
the information generating code is configured to send the information to a wearable computer device and/or a personal computer device associated to the user of the head mounted device; and/or
the information generating code is configured to generate optical function data based at least on the data received from the head mounted device.

The invention also relates to a head mounted device, comprising:
at least one sensor configured to sense at least one feature, and
a communication component configured to communicate data indicative of the at least one feature sensed by the at least one sensor to a monitoring component.

According to further embodiments which can be considered alone or in combination:
the head mounted device further comprises:
a memory storing computer executable codes, and
a processor configured to execute the stored computer executable codes so as to generate an information indicative of the relative position of the head mounted device and the user of the head mounted device based at least on the feature sensed by the at least one sensor; and/or
the least one sensor is configured to sense at least one feature indicative of the relative position of the head mounted device and at least one reference point of the head of the user of the head mounted device; and/or
the head mounted device further comprises a display device configured to display information to the user and to position the displayed image based on the relative position of the head mounted device and the user of the head mounted device; and/or
the head mounted device further comprises an optical function controller adapted to control the optical function of the head-mounted device, and wherein the computer executable codes when executed by the processor generate optical function data based at least on the feature sensed by the at least one sensor, the optical function data being received by the optical function controller so as to adapt the optical function of the head-mounted device; and/or
the at least one sensor is a capacitive sensor configured to sense a contact between the skin of the user, for example the user's head, and the head mounted device; and/or
at least one sensor is a time of flight sensor configured to sense the distance between the head mounted device and the user of the head mounted device, for example the user's head; and/or
at least one sensor is a camera configured to sense the distance between the head mounted device and the user of the head mounted device, for example the user's head; and/or at least one sensor is a proximity sensor based on infrared reflectance on the user skin so as to sense the proximity between the head mounted device and the user of the head mounted device, for example the user's head; and/or at least one sensor is an accelerometer and/or gyroscope configured to sense the orientation and position and variation of orientation and position of the head mounted device.

According to a further aspect, the invention relates to a system, comprising:
a head mounted device, comprising:
at least one sensor configured to sense at least one feature,
a communication component configured to communicate data indicative of the at least one feature sensed by the at least one sensor of the head mounted device, and
a monitoring component, external to the head mounted device, according to the invention.

The invention further relates to a method for monitoring the relative position of a head mounted device and a user of the head mounted device, the head mounted device comprising at least one sensor, the method comprising:
head mounted data receiving step during which data from the head mounted device indicative of at least one feature sensed by the at least one sensor of the head mounted device are received,
an information generating step during which an information indicative of the relative position of the head mounted device and the user of the head mounted device is generated based at least on the data received from the head mounted device.

The invention also relates to a monitoring method for monitoring the relative position of a head mounted device and a user of the head mounted device, the head mounted device comprising at least one sensor, the method comprising:
a data receiving step during which data are received from the head mounted device indicative of at least one feature sensed by the at least one sensor of the head mounted device,
an information generating step during which an information indicative of the relative position of the head mounted device and the user of the head mounted device is generated based at least on the data received from the head mounted device.

According to further embodiments which can be considered alone or in combination:
the method further comprises a storing step during which the received data are stored over time and the information is indicative of the evolution over time of the relative position of the head mounted device and the user of the head mounted device; and/or
the information is generated using statistical analysis of the data received from the head mounted device and stored over time; and/or
the information generated during the information generating step comprises a recommendation data generated based at least on the data received from the head mounted device; and/or
the recommendation data includes a lens design recommendation; and/or
the recommendation data includes an ophthalmic lens recommendation; and/or
the recommendation data includes an alert indicative of wearer's vision state; and/or
the recommendation data includes an activation of at least one functionality on the head mounted device; and/or
the recommendation data includes an access to a service offer; and/or the method further comprises a data sending step during which the information generated during the information generating step is sent to a wearable computer device and/or a personal computer device associated to the user of the head mounted device; and/or
the information generated during the information generating step comprises optical function data generated based at least on the data received from the head mounted device.

The invention further relates to a computer program product comprising one or more stored sequences of instructions that are accessible to a processor and which, when executed by the processor, causes the processor to carry out the steps of the method according to the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method.

The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Elements in the figures are illustrated for simplicity and clarity and have not necessarily been drawn to scale. For example, the dimensions of some of the elements in the figure may be exaggerated relative to other elements to help improve the understanding of the embodiments of the present invention.

Figures 1, 2:
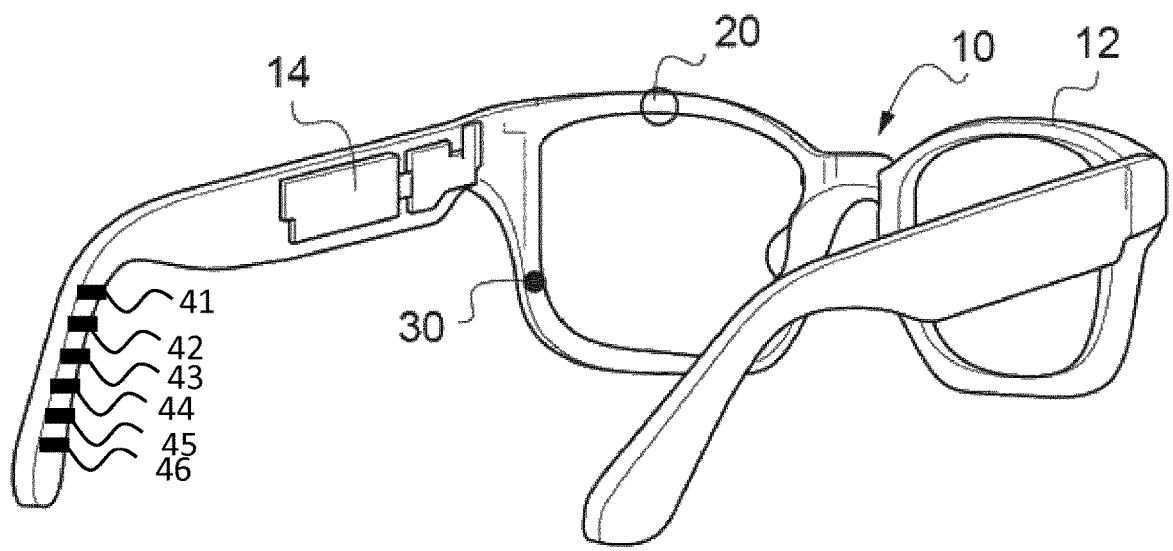
FIG. 1 is a schematic representation of an head mounted device according to an embodiment of the invention.
FIG. 2 is a table illustrating the use of capacitive sensors.

FIG. 1 represents an example of head-mounted device 10 comprising sensors 20, 30, 41 to 46 and a communication component 14. The head mounted device 10 comprises a spectacle frame 12 and the sensors and communication unit are mounted on the spectacle frame 12.

Although the invention is not limited to such type of head-mounted device, it appears to be particularly advantageous for head mounted devices comprising a spectacle frame.

Indeed, such type of head mounted device is more likely to move relative to the user and therefore monitoring the relative position of the head mounted device may be greatly advantageous.

The head mounted device 10 represented on FIG. 1 comprises a spectacle frame 12 with sensors 20 and 30, directed at the left side of the wearer's head (not shown). The sensors 20 and 30 are arranged to be directed toward the head in order to track for example the distance between the sensor and the head of the user.

At least one of the sensors 20, 30 is configured to sense at least one feature indicative of the relative position of the head mounted device and at least one reference point of the head of the user of the head mounted device.

Such reference point is preferably immobile with reference to the head of the wearer. Typically, the reference point may be ear base or eyebrow.

At least one of the sensors may be a time of flight sensor configured to sense the distance between the head mounted device and the user of the head mounted device, for example the user's head. Such sensor may be placed on the frame in such position that when the head mounted device is worn by the user the sensor points to the face of the wearer. The sensor typically uses time of flight (TOF) technology and is arranged to provide data indicative of the distance to the head depending of the position of the head mounted device.

According to an embodiment of the invention, at least one sensor is a proximity sensor based on infrared reflectance on the user skin so as to sense the proximity between the head mounted device and the user of the head mounted device, for example the user's head.

Such infrared reflectance sensor may advantageously be placed on the nose bridge of the frame of the head mounted device and oriented toward the nose so as to provide data indicative of the distance to the skin of the user, for example of the sellion of the user. Advantageously, when the head mounted device is worn by the user, the nose bridge sensor is very close to the skin of the user, and if the position of the head mounted device changes this distance increases and can be easily detected.

The time of flight and the infrared reflectance sensors may require training to detect distance during the different use of the head mounted device, and detection of the different positions occur after statistical analysis of the data provided by the sensors.

According to an embodiment of the invention, at least one sensor is a capacitive sensor configured to sense a contact between the skin of the user, for example the user's head, and the head mounted device.

Advantageously, capacitive sensors can detect skin and use very low power.

As represented on FIG. 1, a group of capacitive sensors, about 2 mm each, may be inserted in the frame of the head mounted device, for example at the ear level.

Using a plurality of capacitive sensors can provide information concerning the position of the head mounted device.

According to a further embodiment of the invention, at least one sensor is an accelerometer and/or gyroscope configured to sense the orientation of the head mounted device.

Typically, in a first reference position, the head mounted device is almost horizontal, and in other position the head mounted device may be oriented upward or downward, this inclination can be measured by 3 or 6 axis sensors commonly used in mobile phone. Typically, a 3 axis accelerometer can provide data concerning the horizontality of the head mounted device and a 3 axis gyroscope can provide data concerning rotation of the head mounted device. Also the movements of the head mounted device from one position to another can be detected, and differentiated from head movement to be sure to detect a head mounted device relative movement. In some case only accelerometer can be used, to save power.

The different type of sensors provide features indicative that need to be processed so as to determine information indicative of the relative position of the head mounted device and the user of the head mounted device.

For example, the capacitive sensors provide data indicative of a distance between each sensor and the skin of the user. As such the data can be thresholded to only provide a binary indication relating to the contact or not of the sensor with the sink of the user.

Typically, by processing data provided by a number of capacitive sensors, as represented on FIG. 1, one can provide information indicative of the relative position of the head mounted device and the user of the head mounted device.

For example considering the six capacitive sensors of FIG. 1, such configuration allows determining the position of the head mounted device relative to the ear of the user, and so detect if the head mounted device is worn or not (all the sensors are inactive if not worn). Such configuration also allows detecting if the head mounted device is turned up or down, because different sensors detect the contact with the skin of the user depending of the position of the head mounted device.

As illustrated in FIG. 2, when the head mounted device is worn normally, the middle capacitive sensors 43, 44 and 45 detect skin contact and the other capacitive sensors 41, 42, and 46 detect no skin contact.

When the head mounted device is in an upward position, the front capacitive sensors 42, 43 and 44 detect skin contact and the other capacitive sensors 41, 45 and 46 detect no skin contact.

When the head mounted device is in downward position, the rear capacitive sensors 44, 45 and 46 detect skin contact and the other capacitive sensor detect no skin contact.

When the head mounted device is not worn by the user, all the capacitive sensors 41 to 46 detect no skin contact.

A capacitive sensor may be positioned at the bridge nose level, to measure distance to the wearer skin.

The data issued by the capacitive sensors may be used in a more complete manner that simply detecting if the each sensor is in contact or not with the skin of the wearer. For example, the data provided by the capacitive sensors may be processed to provide information relative to the distance between each sensor and the skin of the user.

The monitoring of the relative position of the head mounted device and the user requires having a communication unit 14 configured to communicate data indicative of the at least one feature sensed by the at least one sensor to a monitoring component.

The monitoring component typically comprises:
a memory configured to store computer executable code, and
a processor configured to execute the following computer executable codes stored in the memory:
a communication code configured to receive data from the head mounted device indicative of at least one feature sensed by the at least one sensor of the head mounted device,
an information generating code configured to generate an information indicative of the relative position of the head mounted device and the user of the head mounted device based at least on the data received from the head mounted device.

The monitoring component may be integrated in the head mounted device so as to have an embedded system.

Typically, the head mounted device further comprises:
a memory storing computer executable codes, and
a processor configured to execute the stored computer executable codes so as to generate an information indicative of the relative position of the head mounted device and the user of the head mounted device based at least on the feature sensed by the at least one sensor of the head mounted device.

Although not represented, the head mounted device may further comprise a power source, for example a battery and/or other electronics.

Figure 3:
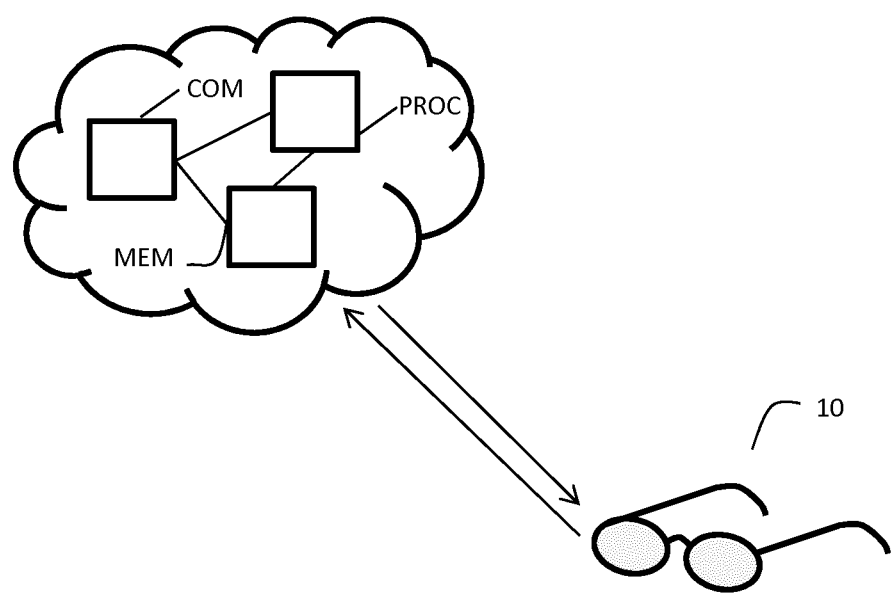
FIG. 3 represents a networked data-processing device according to the invention.

According to an embodiment of the invention, illustrated on FIG. 3, the head mounted device communicates with a distant entity that comprises a monitoring component. Communication can be done through different communication devices and protocols, like Bluetooth, Zigbee, WiFi or others.

For example, the communication unit is configured to communicate with the distance entity either to store the measured features in a memory MEM or to provide an information indicative of the relative position of the head mounted device and the user of the head mounted device.

Typically, the distance entity comprises a communication unit COM configured to communicate at least with the head mounted device, a memory MEM, at least one processor PROC and program instructions stored on a non-transitory computer-readable medium and executable by the at least one processor to generate an information indicative of the relative position of the head mounted device and the user of the head mounted device based at least on the feature sensed by the at least one sensor of the head mounted device.

The distance entity can include different computing objects such as personal digital assistants, audio/video devices, mobile phones, MPEG-1 Audio Layer 3 (MP3) players, personal computers, laptops, tablets, bluetooth headset, watch, wristband, etc. . . . .

Each computing object and the head mounted device can communicate with one or more other by way of a communication network, either directly or indirectly. Even though illustrated as a single element in FIG. 3, network can include other computing objects and computing devices that provide services to the system of FIG. 3, and/or can represent multiple interconnected networks, which are not shown.

In a network environment in which the communications network/bus can be the Internet, the computing objects can be Web servers, file servers, media servers, etc. with which the client computing objects or devices communicate via any of a number of known protocols, such as the hypertext transfer protocol (HTTP).

According to an embodiment of the invention, the data received by the monitoring component from the communication unit may be stored over time and the information is indicative of the evolution over time of the relative position of the head mounted device and the user of the head mounted device.

Furthermore the information generating code may be configured to generate information using statistical analysis of the data received from the head mounted device and stored over time.

Statistics involves the collection, organization, analysis, interpretation, and/or presentation of measured/collected information. With advances in technology, more extensive and complex computing allows massive amounts of data to be collected, stored and/or processed. Further, methods for evaluating the data are numerous.

Statistical analysis can be employed to process and/or evaluate information sensed.

Typically, statistical analysis is advantageous to verify that the relative position is maintained during a few seconds to be sure it is not only a user movement, in particular a head movement, but a movement of the head mounted device relative to the user.

For example, by correlating head mounted device movement detected by accelerometer with distance measurement from a capacitive sensor, one can have a reliable detection of the head mounted device position changes relatively to the user, in particular the head of the user. In this case this position change can be used for further head position measurement, to calibrate again the head horizontal position.

According to an embodiment of the invention, the information generating code is configured to provide a recommendation data based at least on the data received from the head mounted device.

Typically, the recommendation data includes a lens design recommendation and/or an ophthalmic lens recommendation and/or an alert indicative of wearer's vision state and/or an activation of at least one functionality on the head mounted device and/or an access to a service offer.

Typically, according to an embodiment, the head mounted device comprises an optical function controller adapted to control the optical function of the head-mounted device. The computer executable codes stored in the memory of the monitoring component when executed by the processor generate optical function data based at least on the feature sensed by the at least one sensor, the optical function data being received by the optical function controller so as to adapt the optical function of the head-mounted device.

Advantageously, the optical function of the head mounted device can be adapted based on the relative position of the head mounted device and the user.

For example, upon detection that the head mounted device has slipped along the nose of the user, the optical function, in particular the position of the near and far vision zone, may be adjusted to the new position of the head mounted device relative to the user.

Figure 4:
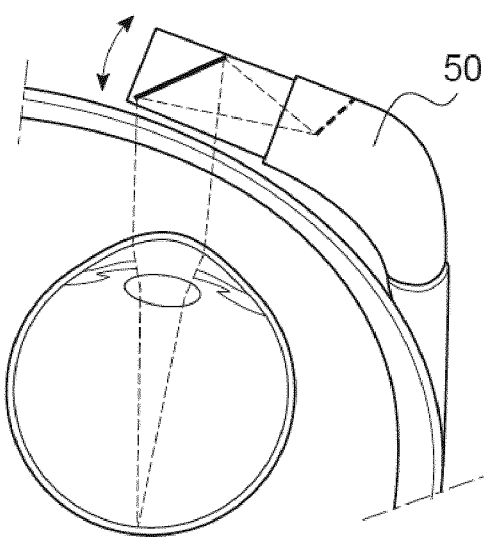
FIG. 4 is a schematic representation of a head mounted device according to a further embodiment of the invention.

As represented on FIG. 4, the head mounted device according to the invention may comprise a virtual image display device 50, preferably allowing the wearer to see both the virtual image and the real world through it. The virtual image display device is able to display graphical images, and an electronic driving system (memory+processor) sends to the virtual display image the image to display. Preferably it is able to display image in different viewing directions, and this displaying direction and the position of the field of view, can be adapted from the relative position measured by the sensors. Furthermore, the image to be displayed can be modified depending of the position measured by the sensors.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A monitoring component for monitoring relative position of a head mounted device and a user of the head mounted device, the head mounted device including at least one sensor, the monitoring component comprising:
    a memory configured to store computer executable code; and
    a processor configured to execute computer executable codes stored in the memory of:
        a communication code configured to receive data from the head mounted device indicative of at least one feature sensed by the at least one sensor of the head mounted device,
        an information generating code configured to generate an information indicative of the relative position of the head mounted device and the user of the head mounted device based at least on the data received from the head mounted device;
    wherein the information generating code is configured to provide a recommendation data based at least on the data received from the head mounted device, and
    wherein the recommendation data includes a lens design recommendation.

2. The monitoring component according to claim 1, further comprising a memory in which the received data is stored over time and the information is indicative of evolution over time of the relative position of the head mounted device and the user of the head mounted device.

3. The monitoring component according to claim 1, wherein the information generating code is configured to generate information using statistical analysis of the data received from the head mounted device and stored over time.

4. The monitoring component according to claim 1, wherein the recommendation data includes an ophthalmic lens recommendation.

5. The monitoring component according to claim 1, wherein the recommendation data includes an alert indicative of wearer's vision state.

6. The monitoring component according to claim 1, wherein the recommendation data includes an activation of at least one functionality on the head mounted device.

7. The monitoring component according to claim 1, wherein the recommendation data includes an access to a service offer.

8. The monitoring component according to claim 1, wherein the information generating code is configured to send the information to a wearable computer device and/or a personal computer device associated to the user of the head mounted device.

9. A system, comprising:
    a head mounted device, comprising:
        at least one sensor configured to sense at least one feature,
        a communication component configured to communicate data indicative of the at least one feature sensed by the at least one sensor of the head mounted device; and
    a monitoring component, external or integrated to the head mounted device, according to claim 1.

10. The monitoring component according to claim 1, wherein the information generating code is configured to generate optical function data based at least on the data received from the head mounted device.

11. A head mounted device, comprising:
    at least one sensor configured to sense at least one feature;
    a communication component configured to communicate data indicative of the at least one feature sensed by the at least one sensor to a monitoring component; and
    an optical function controller configured to control an optical function of the head-mounted device, and wherein the computer executable codes when executed by the processor generate optical function data based at least on the feature sensed by the at least one sensor, the optical function data being received by the optical function controller to adapt the optical function of the head-mounted device.

12. The head mounted device according to claim 11, further comprising:
    a memory storing computer executable codes; and
    a processor configured to execute the stored computer executable codes to generate an information indicative of the relative position of the head mounted device and the user of the head mounted device based at least on the feature sensed by the at least one sensor.

13. The head mounted device according to claim 11, wherein the head mounted device further comprises a display device configured to display information to the user and to position the displayed image based on the relative position of the head mounted device and the user of the head mounted device.

14. The head mounted device according to claim 11, wherein the at least one sensor is a capacitive sensor configured to sense a contact between skin of the user and the head mounted device.

15. The head mounted device according to claim 11, wherein at least one sensor is a time of flight sensor and/or a proximity sensor based on infrared reflectance on the user skin and/or a camera configured to sense distance between the head mounted device and the user of the head mounted device.

16. The head mounted device according to claim 11, wherein at least one sensor is an accelerometer and/or gyroscope configured to sense movement and/or orientation of the head mounted device.

17. The head mounted device according to claim 11, wherein the optical function controller is further configured to adjust a position of a near and far vision zone of the head mounted device to a new position of the head mounted device.

18. A monitoring method for monitoring relative position of a head mounted device and a user of the head mounted device, the head mounted device including at least one sensor, the method comprising:
- a data receiving during which data is received from the head mounted device indicative of at least one feature sensed by the at least one sensor of the head mounted device;
- an information generating during which an information indicative of the relative position of the head mounted device and the user of the head mounted device is generated based at least on the data received from the head mounted device;
- wherein the information generated during the information generating comprises a recommendation data generated based at least on the data received from the head mounted device; and
- wherein the recommendation data includes a lens design recommendation.

19. The monitoring method according to claim 18, further comprising a storing during which the received data is stored over time and the information is indicative of evolution over time of the relative position of the head mounted device and the user of the head mounted device.

20. The monitoring method according to claim 18, wherein the information is generated using statistical analysis of the data received from the head mounted device and stored over time.

21. The monitoring method according to claim 18, further comprising a data sending during which the information generated during the information generating is sent to a wearable computer device and/or a personal computer device associated to the user of the head mounted device.

22. The monitoring method according to claim 18, wherein the information generated during the information generating comprises optical function data generated based at least on the data received from the head mounted device.

23. The monitoring method according to claim 18, wherein the recommendation data includes an ophthalmic lens recommendation.

24. The monitoring method according to claim 18, wherein the recommendation data includes an alert indicative of wearer's vision state.

25. The monitoring method according to claim 18, wherein the recommendation data includes an activation of at least one functionality on the head mounted device.

26. The monitoring method according to claim 18, wherein the recommendation data includes an access to a service offer.

* * * * *